United States Patent [19]

Chys

[11] Patent Number: 5,686,647
[45] Date of Patent: Nov. 11, 1997

[54] PROCESS FOR THE PREPARATION OF UREA

[75] Inventor: Jan Chys, Mariakerke, Belgium

[73] Assignee: Norsk Hydro a.s, Oslo, Norway

[21] Appl. No.: 529,602

[22] Filed: Sep. 18, 1995

[30] Foreign Application Priority Data

Nov. 18, 1994 [EP] European Pat. Off. ............ 94203153

[51] Int. Cl.⁶ ............................................... C07C 273/04
[52] U.S. Cl. ............................ 564/67; 504/327; 564/73
[58] Field of Search ........................ 564/67, 73; 504/327

[56] References Cited

U.S. PATENT DOCUMENTS 4,411,683 10/1983 Goertz ............................................ 71/28

FOREIGN PATENT DOCUMENTS 722434  1/1955  United Kingdom.
1049464 11/1966  United Kingdom.

Primary Examiner—Shailendra Kumar
Attorney, Agent, or Firm—Wenderoth, Lind & Ponack

[57] ABSTRACT

Process for the preparation of urea, wherein in a first step ammonia and carbon dioxide react in suitable conditions so as to form a first mixture containing a quantity of urea, wherein in one or more subsequent steps ammonia and carbon dioxide are removed from the first mixture and the obtained urea is concentrated until a urea concentration has been reached suitable to be granulated in a gas stream, whereby apart from urea granules a second mixture containing air, gaseous ammonia and urea dust is formed which subsequently is washed, and wherein before or during the washing an amount of formaldehyde is added to the second mixture of air, ammonia and urea under circumstances wherein the ammonia can react with the formaldehyde in order to form hexamethylenetetramine (HMTA) whereupon the so formed HMTA is separated from the gas stream and is returned into the process before the granulation step.

6 Claims, 2 Drawing Sheets

PROCESS FOR THE PREPARATION OF UREA

BACKGROUND OF THE INVENTION

1. Field of Invention

The invention relates to a process for the preparation of urea, wherein in a first step ammonia and carbon dioxide react in suitable conditions so as to form a first mixture containing a quantity of urea, wherein in one or more subsequent steps ammonia and carbon dioxide are removed from the first mixture and the obtained urea is concentrated until a urea concentration has been reached suitable to be granulated in a gas stream, whereby apart from urea granules, a second mixture containing air, gaseous ammonia and urea dust is formed which subsequently is washed.

2. Description of Prior Art

Such a process is generally known and described e.g. in the magazine "Nitrogen" nr. 66 of March–April 1970, page 17-22 "Urea processes today". Practically it has been found that by the washing of the concentrated second mixture of air, gaslike ammonia and urea dust the ammonia which is present in this mixture cannot be removed in a sufficient way and is therefore dragged along in the environmental air, which means an additional charge to the environment.

SUMMARY OF THE INVENTION

It is therefore an object of the invention to provide a process of the above identified type, wherein the amount of emitted ammonia is reduced in a substantial way.

According to the invention this object is achieved in that before or during the washing an amount of formaldehyde is added to the second mixture of air, ammonia and urea, under circumstances wherein the ammonia can react with the formaldehyde in order to form hexamethylenetetramine (HMTA), whereupon the so formed HMTA is separated from the gas stream and is returned into the process before the granulation step.

DETAILED DESCRIPTION OF THE INVENTION

Is has been found that through the addition of formaldehyde the gaseous ammonia is chemically bound in a substantial way by the formaldehyde by forming a compound which can easily be removed from the gas phase.

It has to be noted that as such it is known that before the granulation of urea, formaldehyde is added thereto in order to improve the granulation process.

This addition of formaldehyde is not able to reduce the emission of ammonia after the granulation and the washing. It has also been found that by the recycling of the HMTA which is formed according to the invention into the process before the granulation step and by adequately selecting the process circumstances where the HMTA is re-introduced, the HMTA is decomposed into ammonia and formaldehyde. Thus the ammonia can be returned into the process in a very effective way and the introduction of formaldehyde in the process in this way reduces the amount of the formaldehyde needed for the granulation step.

Other characteristics and advantages of the invention will become clear from the following description wherein reference has been made to the annexed drawings.

Figure 1:
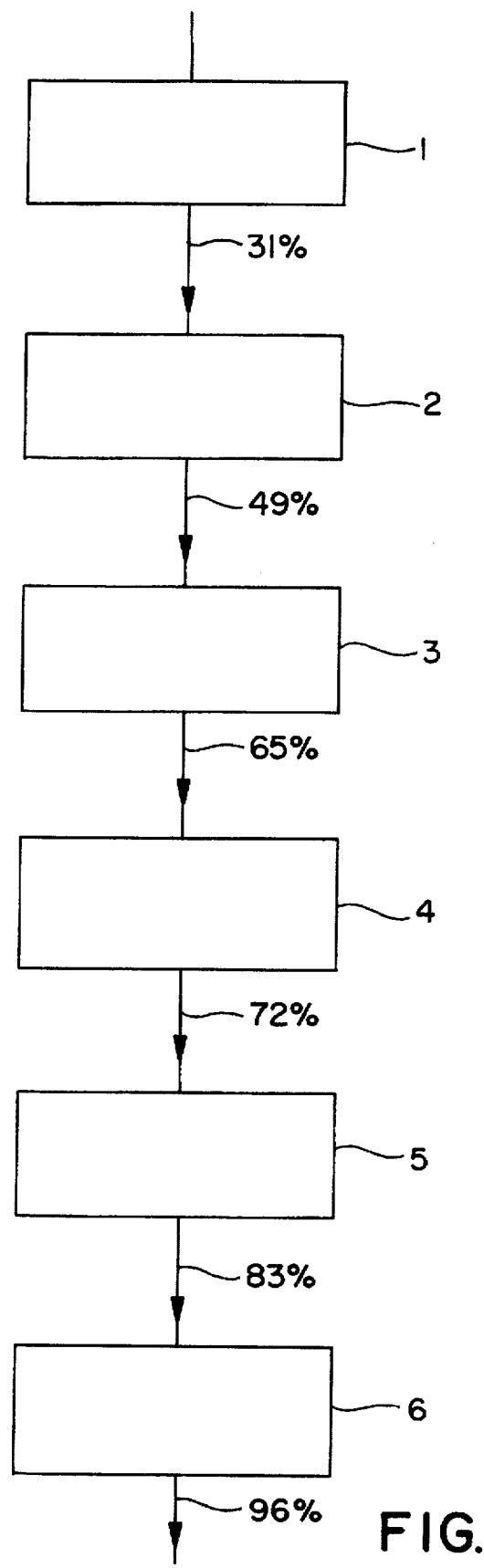
FIG. 1 is a block scheme of the urea process before the granulation.

In the urea process such as represented schematically in FIG. 1 in phase 1, the reaction phase, block 1, a mixture of ammonia and carbon dioxide (molar relationship 2:1) is formed in a high pressure reactor under a pressure of e.g. 200 bar at a temperature of 190° C. Under these circumstances this mixture reacts to form a reaction mixture comprising urea (31% by weight), water and carbamate.

In a next phase (block 2) of the process the reaction mixture is brought into circumstances with reduced pressure. Typical values are e.g. 190° C. and 70 bar. In these circumstances it is possible to remove a part of the formed carbamate from the process stream, such that a reaction mixture with e.g. 49% by weight urea is formed.

In the next phase (block 3) the pressure is once again reduced and the reaction mixture is brought to a pressure of e.g. 12 bar and a temperature of 165° C. By again removing a part of the carbamate, a reaction mixture with e.g. 65 by weight % urea is obtained.

In the next phase (block 4) the pressure and the temperature are once again reduced to values of about 3.5 bar and 125° C. In these circumstances the carbamate is substantially decomposed into carbon dioxide and ammonia and can be removed in this form. The result is a further increase of urea concentration in the reaction mixture to a value of e.g. 72% by weight.

Subsequently the pressure is once again reduced to a value of about 1.5 bar and the temperature can be set to 120° C. (block 5). In these circumstances not only ammonia and carbon dioxide are removed from the reaction mixture, but also water is evaporated. The concentration of urea can thereby increase to e.g. 83% by weight.

In a next step (block 6) at last the pressure is still further reduced to about 0.35 bar, at a temperature of 133° C. Thereby the ammonia, carbon dioxide and water are still further removed from the reaction mixture. The urea concentration can thereby increase to a value of e.g. 96% by weight, a concentration which is extremely adapted to a granulation in an air stream.

Figure 2:
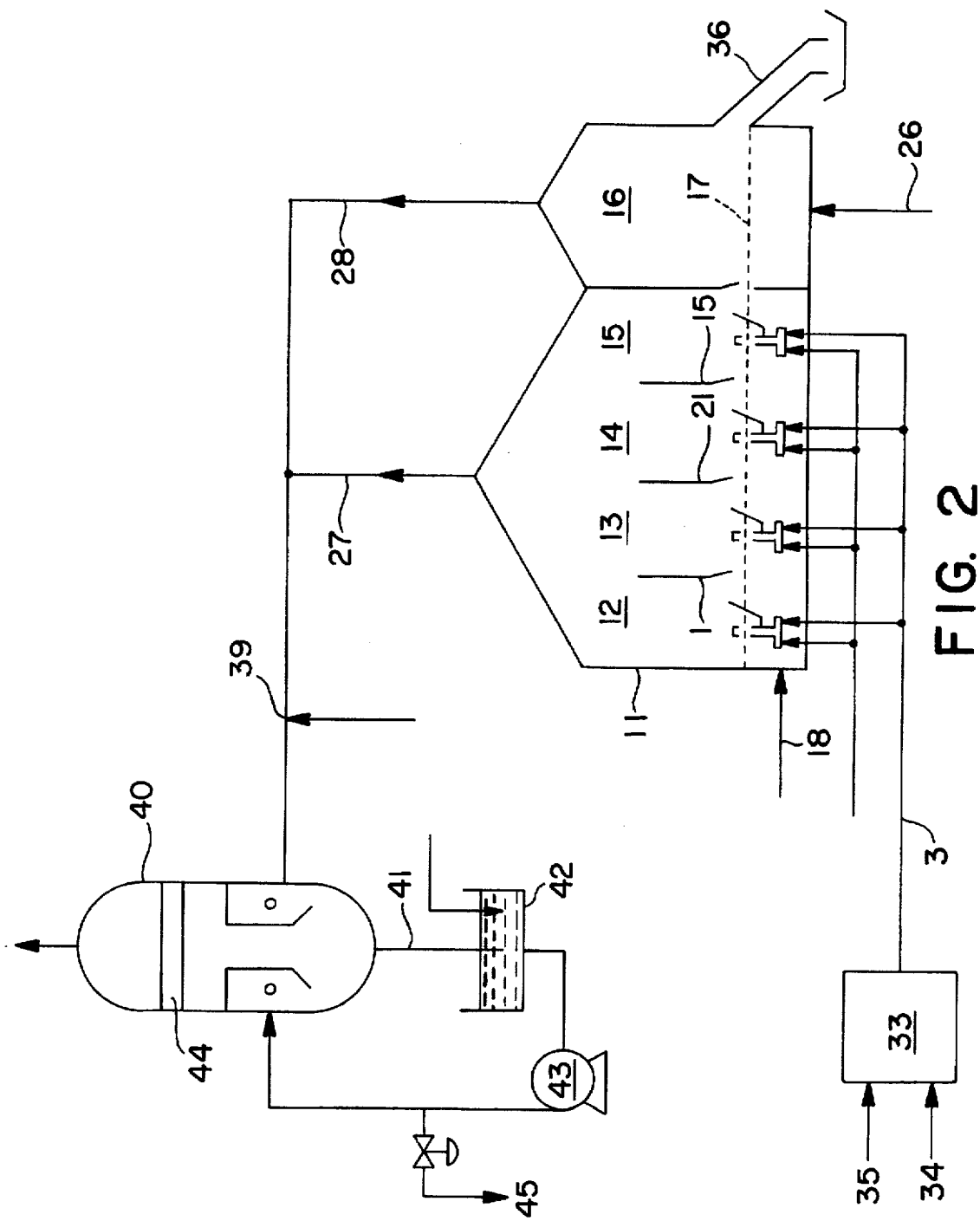
FIG. 2 is a schematic representation of the granulation process with the addition of formaldehyde according to the invention.

In FIG. 2 the granulation step is schematically represented, which granulation is based upon the principle of "fluid bed" granulation such as described in the Dutch patent application 78061213.

In FIG. 2 there is represented a granulator 11 which is divided into a plurality of compartments 2, 3 and 4 for the granulation and compartments 15 and 16 for subsequent cooling and drying of the urea particles. The granulator 1 contains a grid 17, which carries the fluidised bed and transmits the air of fluidisation, preheated in one or more heaters (not shown) and supplied through conduit 18. The space below the grid 17, can be divided in the same way as the space above it, in which case the air of fluidisation is applied separately to each of these compartments. The granulator 1 is further provided at the bottom with pneumatic sprayers 19, 20 and 21 which extend to a level above grid 17. It is also possible to use one or more sprayers in each compartment. The urea solution supplied through conduit 23, is mixed with spraying air supplied through conduit 24 and sprayed into the compartments 12, 13 and 14. The urea solution supplied to conduit 23 is originating from a vessel 33, wherein the urea solution originating from the process as described above is supplied through conduit 34. In this vessel a granulation additive is also added through conduit 35. The base of this granulation additive can be formaldehyde but in the process shown one is using a solution of urea and formaldehyde; e.g. 57% by weight formaldehyde and 25% by weight urea and water, whereby in the chosen process circumstances of 130° C. methylene diurea is formed.

The fluid bed is formed by urea nuclei. For subsequent conditioning, cooling and if needed drying of the granules in the compartments 15 and 16 air can be used supplied through conduit 26. The granulator 11 further contains an outlet 36 for the urea granules which subsequently can be treated in different ways.

The air and the dragged along urea dust and gaseous ammonia are discharged through outlet 27 and 28. According to the invention a mixture of formaldehyde, water and optional by urea, is added to this mixture. This takes place at location 39 just before the washing device 40; By evaporation of the added water, the temperature of this gaseous mixture is reduced. It is accepted that under these reaction circumstances formaldehyde can react with gaseous ammonia in order to form hexamethylenetetramine. A reaction of formaldehyde with urea is not so easy under these circumstances as urea is still solid and has a very low reactivity therefor.

The mixture with added formaldehyde is transferred into the washing device 40 and is washed with a aqueous urea solution of e.g. 40% urea. The formed hexamethylene tetramine and the urea dust are removed in a substantial way by the liquid phase and transported through a conduct 41 to a reservoir 42. Through a pump 43 this mixture can be reintroduced into the washing device 20. The gas, after having passed a droplet catcher 44 and if needed a further purifying device, is vented into the environment.

The urea solution used for the washing in reservoir 42 and charged with hexamethylene tetramine is partially reintroduced into the above described urea process through conduit 45. Basically this mixture, after being brought to the right pressure and temperature, may be recycled in every phase of the process. Practically it has been found that from the energy standpoint the most advantage arises when it is reintroduced in the above described process in block 5, i.e. at a pressure of 1.5 bar and a temperature of 110° C.

The formaldehyde introduced in this way in the process can be deducted from the formaldehyde which is introduced to conduit 35. The advantage and characteristics of the invention will be illustrated by the following examples.

EXAMPLE 1

In a process such as described above after granulation formaldehyde is dosed in a quantity indicated in table 1. According to this example the addition of formaldehyde takes place at the location of the droplet catcher in the washing device 40 by means of an aqueous formaldehyde solution of 37%. The amount used is indicated in column 1 of table 1. The amount of ammonia in the air stream after the washing device is indicated in column 2.

EXAMPLE II

Example I is repeated with an addition of formaldehyde before the washing device. The results are listed in table 1.

EXAMPLE III

Example II is repeated but instead of formaldehyde to be added a solution of 57% of formaldehyde and 23% of urea in water is added to the washing device. The results are listed in table I.

TABLE 1

|  |  | Dose formaldehyde kg/ton urea | $NH_3$ in gasstream kg/ton urea |
|---|---|---|---|
| Example I | A | 0 | 0.58 |
|  | B | 4.4 | 0.41 |
|  | C | 6.0 | 0.46 |
| Example II | A | 0 | 0.55 |
|  | B | 3.8 | 0.33 |
|  | C | 7.7 | 0.13 |
| Example III | A | 0 | 0.57 |
|  | B | 4.6 | 0.26 |
|  | C | 6.1 | 0.33 |
|  | D | 8.2 | 0.27 |

From table 1 it is clear that the amount of ammonia in the vented gas is reduced in a substantial way, especially if the formaldehyde is added to the mixture before the washing device.

Furthermore it has been found that the amount of formaldehyde in the vented gas is only increased in a very slight way and is still far below the allowed values.

The dust content of the vented gas has not been influenced.

It is clear that there has been described a very specific urea process and a very specific granulation process, but that the invention is not restricted to these processes. Especially another reaction and concentration process for the urea can be used as long as this is based upon the synthesis of ammonia and carbon dioxide. Furthermore the application of the invention is not restricted to the granulation process by means of a so-called "fluid bed" process. Especially it is possible to obtain urea granules through prilling and use formaldehyde as well.

I claim:

1. A process for preparing urea, which comprises:

reacting ammonia and carbon dioxide to form a first mixture containing urea, ammonia and carbon dioxide, removing ammonia and carbon dioxide from the first mixture and concentrating the urea to a urea concentration suitable for granulation in a gas stream, granulating the concentrated urea to form urea granules and a second mixture containing air, gaseous ammonia and urea dust, and washing the second mixture, wherein before or during the washing an amount of formaldehyde is added to the second mixture under conditions wherein the ammonia in the second mixture reacts with the formaldehyde to form hexamethylenetetramine, and the hexamethylenetetramine is separated and returned into the process before the granulation step.

2. A process according to claim 1, wherein the second mixture originating from the granulation is washed by means of an aqueous solution of urea.

3. A process according to claim 1, wherein the formaldehyde is added to the second mixture before washing with an aqueous solution of urea.

4. A process according to claim 1, wherein the hexamethylenetetramine is incorporated in an aqueous solution of urea and is returned together with this solution into the process before the granulation.

5. A process according to claim 4, wherein the aqueous solution of urea charged with hexamethylenetetramine is returned into the process in a phase wherein the first mixture is substantially under normal atmospheric conditions.

6. A process according to claim 1, wherein for each ton of urea produced 3 to 10 kg of formaldehyde is added to the second mixture before or during the washing.

* * * * *